(12) United States Patent
Bosua et al.

(10) Patent No.: US 12,146,841 B2
(45) Date of Patent: Nov. 19, 2024

(54) NON-INVASIVE ANALYTE SENSOR WITH TEMPERATURE COMPENSATION

(71) Applicant: Know Labs, Inc., Seattle, WA (US)

(72) Inventors: Phillip Bosua, Seattle, WA (US); Edward Stephen Lowe, Jr., Seattle, WA (US)

(73) Assignee: KNOW LABS, INC., Seattle, WA (US)

( * ) Notice: Subject to any disclaimer, the term of this patent is extended or adjusted under 35 U.S.C. 154(b) by 140 days.

(21) Appl. No.: 17/805,338

(22) Filed: Jun. 3, 2022

(65) Prior Publication Data

US 2023/0145527 A1 May 11, 2023

Related U.S. Application Data

(63) Continuation-in-part of application No. 17/454,383, filed on Nov. 10, 2021.

(51) Int. Cl.
| | |
|---|---|
| *G01N 22/00* | (2006.01) |
| *G01K 13/10* | (2006.01) |
| *G01N 33/49* | (2006.01) |
| *G01N 33/76* | (2006.01) |

(52) U.S. Cl.
CPC .......... *G01N 22/00* (2013.01); *G01K 13/10* (2013.01); *G01N 33/49* (2013.01); *G01N 33/76* (2013.01)

(58) Field of Classification Search
CPC ........ G01N 22/00; G01N 33/49; G01N 33/76; G01K 13/10; G01K 1/026
See application file for complete search history.

(56) References Cited

U.S. PATENT DOCUMENTS

| | | | |
|---|---|---|---|
| 6,359,444 B1* | 3/2002 | Grimes | G01N 22/00 324/633 |
| 7,295,827 B2 | 11/2007 | Liu et al. | |
| 8,223,021 B2 | 7/2012 | Goodnow et al. | |
| 8,682,615 B2* | 3/2014 | Hayter | G16H 40/67 702/183 |
| 9,041,920 B2 | 5/2015 | Mander et al. | |
| 9,198,607 B2 | 12/2015 | Fischer | |
| 9,316,581 B2 | 4/2016 | Mander et al. | |
| 9,864,024 B2 | 1/2018 | Vester | |
| 10,149,629 B2 | 12/2018 | Szczepaniak et al. | |

(Continued)

FOREIGN PATENT DOCUMENTS

| | | |
|---|---|---|
| EP | 3146898 B1 | 11/2018 |
| EP | 3981329 A1 | 4/2022 |

(Continued)

OTHER PUBLICATIONS

International Search Report and Written Opinion issued for International Patent Application No. PCT/IB2022/060799, Date of mailing: Feb. 21, 2023, 7 pages.

(Continued)

*Primary Examiner* — Akm Zakaria

(74) *Attorney, Agent, or Firm* — HSML P.C.

(57) ABSTRACT

A non-invasive analyte sensor includes one or more temperatures sensors that sense the temperatures of one or more components of the analyte sensor. The sensed temperature(s) can be used to post-process (i.e. correct) the data collected by the analyte sensor and/or used to adjust operation of the analyte sensor.

4 Claims, 7 Drawing Sheets

(56) References Cited

U.S. PATENT DOCUMENTS

| | | |
|---|---|---|
| 10,478,101 B1 | 11/2019 | Cespedes et al. |
| 10,548,503 B2 | 2/2020 | Bosua |
| 10,617,296 B2 | 4/2020 | Sloan et al. |
| 10,856,766 B2 | 12/2020 | Leabman |
| 10,912,500 B2 | 2/2021 | Poeze et al. |
| 10,956,950 B2 | 3/2021 | Al-Ali et al. |
| 11,031,970 B1 | 6/2021 | Bosua |
| 11,033,208 B1 | 6/2021 | Bosua |
| 11,058,317 B1 | 7/2021 | Bosua |
| 11,058,321 B2 | 7/2021 | Hein |
| 11,058,331 B1 | 7/2021 | Bosua |
| 11,063,373 B1 | 7/2021 | Bosua |
| 11,202,582 B2 | 12/2021 | Verkruijsse et al. |
| 11,234,619 B2 | 2/2022 | Bosua |
| 11,244,753 B2 | 2/2022 | Haggerty et al. |
| 11,291,374 B2 | 4/2022 | Lee et al. |
| 11,298,037 B2 | 4/2022 | Leabman |
| 11,350,830 B2 | 6/2022 | McKenna et al. |
| 11,360,188 B2 | 6/2022 | Leabman |
| 11,367,525 B2 | 6/2022 | Addison et al. |
| 11,389,093 B2 | 7/2022 | Triman et al. |
| 11,426,104 B2 | 8/2022 | Schurman et al. |
| 2003/0036713 A1 | 2/2003 | Bouton et al. |
| 2004/0065158 A1 | 4/2004 | Schrepfer et al. |
| 2004/0127777 A1 | 7/2004 | Ruchti et al. |
| 2004/0133086 A1 | 7/2004 | Ciurczak et al. |
| 2004/0235536 A1 | 11/2004 | Kim et al. |
| 2009/0275814 A1 | 11/2009 | Watanabe et al. |
| 2010/0041969 A1 | 2/2010 | Beise |
| 2011/0028814 A1 | 2/2011 | Petersen et al. |
| 2014/0158535 A1* | 6/2014 | Javitt ............... G01N 27/286 29/601 |
| 2014/0213870 A1 | 7/2014 | Hsu et al. |
| 2014/0357311 A1 | 12/2014 | Suzuki et al. |
| 2016/0051171 A1 | 2/2016 | Pikov et al. |
| 2016/0361002 A1 | 12/2016 | Palikaras et al. |
| 2017/0095667 A1 | 4/2017 | Yakovlev et al. |
| 2017/0181658 A1 | 6/2017 | Dettmann et al. |
| 2018/0028824 A1 | 2/2018 | Pivonka et al. |
| 2018/0064340 A1 | 3/2018 | Hamilton et al. |
| 2018/0357200 A1* | 12/2018 | DeHennis ............ G06F 13/287 |
| 2019/0008422 A1 | 1/2019 | Leath et al. |
| 2019/0053741 A1 | 2/2019 | Chaudhry |
| 2019/0104939 A1 | 4/2019 | Costantine et al. |
| 2019/0269853 A1 | 9/2019 | Doyle et al. |
| 2019/0353752 A1 | 11/2019 | Lin et al. |
| 2019/0357800 A1 | 11/2019 | Bosua |
| 2019/0388000 A1 | 12/2019 | Costantine et al. |
| 2020/0054255 A1 | 2/2020 | Conrad et al. |
| 2020/0057163 A1 | 2/2020 | Bromberg |
| 2020/0146584 A1 | 5/2020 | Bosua |
| 2020/0178800 A1 | 6/2020 | Geissler et al. |
| 2020/0187791 A1 | 6/2020 | Leabman |
| 2020/0187792 A1 | 6/2020 | Leabman |
| 2020/0187793 A1 | 6/2020 | Leabman |
| 2020/0187812 A1 | 6/2020 | Leabman |
| 2020/0187813 A1 | 6/2020 | Leabman |
| 2020/0187814 A1 | 6/2020 | Leabman |
| 2020/0187815 A1 | 6/2020 | Leabman |
| 2020/0187816 A1 | 6/2020 | Leabman |
| 2020/0187817 A1 | 6/2020 | Leabman |
| 2020/0187818 A1 | 6/2020 | Leabman |
| 2020/0187819 A1 | 6/2020 | Leabman |
| 2020/0187820 A1 | 6/2020 | Leabman |
| 2020/0187836 A1 | 6/2020 | Leabman |
| 2020/0187837 A1 | 6/2020 | Leabman |
| 2020/0187867 A1 | 6/2020 | Leabman |
| 2020/0191909 A1 | 6/2020 | Leabman |
| 2020/0191932 A1 | 6/2020 | Leabman |
| 2020/0191933 A1 | 6/2020 | Leabman |
| 2020/0191944 A1 | 6/2020 | Leabman |
| 2020/0191945 A1 | 6/2020 | Leabman |
| 2020/0191947 A1 | 6/2020 | Leabman |
| 2020/0192426 A1 | 6/2020 | Leabman |
| 2020/0192427 A1 | 6/2020 | Leabman |
| 2020/0192428 A1 | 6/2020 | Leabman |
| 2020/0193326 A1 | 6/2020 | Leabman |
| 2020/0195197 A1 | 6/2020 | Leabman |
| 2020/0195293 A1 | 6/2020 | Leabman |
| 2020/0375549 A1 | 12/2020 | Wexler et al. |
| 2021/0186357 A1 | 6/2021 | Bosua et al. |
| 2021/0244308 A1 | 8/2021 | Bosua |
| 2021/0393130 A1* | 12/2021 | DeHennis ............... G16Z 99/00 |
| 2022/0015695 A1 | 1/2022 | Margarito et al. |
| 2022/0031254 A1 | 2/2022 | Al-Ali et al. |
| 2022/0136967 A1* | 5/2022 | Obeng .................... G01N 22/00 435/6.15 |
| 2022/0192494 A1 | 6/2022 | Leabman |
| 2022/0192531 A1 | 6/2022 | Leabman |
| 2022/0248984 A1 | 8/2022 | Poeze et al. |
| 2023/0145527 A1* | 5/2023 | Bosua .................... G01K 13/10 324/633 |

FOREIGN PATENT DOCUMENTS

| | | |
|---|---|---|
| JP | 2012125382 | 7/2012 |
| KR | 1020160081740 | 7/2016 |
| WO | 2017163245 | 9/2017 |
| WO | 2019071138 | 4/2019 |
| WO | 2019198567 | 10/2019 |
| WO | 2019217461 | 11/2019 |
| WO | 2020006077 | 1/2020 |
| WO | 2020037171 | 2/2020 |
| WO | 2021198045 A1 | 10/2021 |
| WO | 2022026623 A1 | 2/2022 |

OTHER PUBLICATIONS

Hanna, J et al., "Noninvasive, wearable, and tunable electromagnetic multisensing system for continuous glucose monitoring, mimicking vasculature anatomy," Science Advances, 6, eaba5320, 2020 (11 pages).

"Contributes to longer healthy life expectancy with non-invasive vital acquisition sensor," Quantum Operation Co., Ltd., presentation found on Jan. 12, 2021 at https://oi.nttdata.com/program/forum/history/20191118/pdf/03_quantum-op.pdf (14 pages including English translation).

International Search Report and Written Opinion for PCT/US2019/031176, mailed Aug. 23, 2019, 9 pages.

Qiang et al., "Quantitative detection of glucose level based on radiofrequency patch biosensor combined with volume-fixed structures," Biosensors and Bioelectronics 98:357-363, 2017.

Shaker, G. et al., "Non-Invasive Monitoring of Glucose Level Changes Utilizing a mm-Wave Radar System," IJMHCI, vol. 10, Issue 3 (2018): pp. 10-29.

Lien, J. et al., "Soli: Ubiquitous Gesture Sensing with Millimeter Wave Radar," ACM Trans. Graph., vol. 35, No. 4, Article 142, 19 pages (Jul. 2016).

International Search Report and Written Opinion issued for International Patent Application No. PCT/IB2020/062222, Date of mailing: Mar. 25, 2021, 7 pages.

* cited by examiner

NON-INVASIVE ANALYTE SENSOR WITH TEMPERATURE COMPENSATION

FIELD

This disclosure relates generally to apparatus, systems and methods of detecting an analyte via spectroscopic techniques using an analyte sensor that includes a detector array (also referred to as an antenna array), wherein the detector array operates in the radio or microwave frequency range of the electromagnetic spectrum.

BACKGROUND

There is interest in being able to detect and/or measure an analyte within a target. One example is measuring glucose in biological material. In the example of measuring glucose in a patient, current analyte measurement methods are invasive in that they perform the measurement on a bodily fluid such as blood for fingerstick or laboratory-based tests, or on fluid that is drawn from the patient often using an invasive transcutaneous device. There are non-invasive methods that claim to be able to perform glucose measurements in biological material. However, many of the non-invasive methods generally suffer from: lack of specificity to the analyte of interest, such as glucose; interference from temperature fluctuations; interference from skin compounds (i.e. sweat) and pigments; and complexity of placement, i.e. the sensing device resides on multiple locations on the patient's body.

SUMMARY

This disclosure relates generally to apparatus, systems and methods of detecting an analyte via spectroscopic techniques using non-optical frequencies such as in the radio or microwave frequency range of the electromagnetic spectrum. An analyte sensor described herein includes a detector array having a plurality of detector elements (also referred to as antenna elements or antennas) at least one of which can transmit an electromagnetic signal in the radio or microwave frequency range and at least one of which can receive an electromagnetic signal in the radio or microwave frequency range resulting from transmission of the electromagnetic signal.

In the non-invasive analyte sensor described herein, one or more temperature sensors may be connected to various elements of the sensor, such as to a circuit board, a radio frequency signal generator, an amplifier, or another element(s) of the sensor. The sensed temperature(s) of the sensor element can be used to post-process (i.e. correct) the data and/or used to adjust operation of the analyte sensor.

In one embodiment, a non-invasive analyte sensor system can include a first antenna that is configured to emit electromagnetic waves in a radio or microwave frequency range, where the first antenna is positioned and arranged to transmit a transmit signal in the radio or microwave frequency range into a target containing at least one analyte; and a second antenna that is configured to detect electromagnetic waves in the radio or microwave frequency range, where the second antenna is positioned and arranged to detect a response in the radio or microwave frequency range resulting from transmission of the transmit signal by the first antenna into the target containing the at least one analyte. Electronic circuitry is provided that includes a transmit circuit that is electrically connectable to the first antenna and that is configured to generate the transmit signal to be transmitted by the first antenna, and a receive circuit that is electrically connectable to the second antenna. There is at least one temperature sensor in the electronic circuitry that detects a temperature of an element of the electronic circuitry.

In another embodiment, an analyte sensor system can include an antenna array having at least three antennas each of which is configured to transmit and receive radio or microwave frequency electromagnetic waves. The sensor system further includes electronic circuitry connected to the antenna array and controlling operation of the at least three antennas so that any one or more of the at least these antennas can be controlled to transmit a transmit signal in a radio or microwave frequency range into a target containing an analyte and so that any one or more of the at least three antennas can be controlled to detect a response in the radio or microwave frequency range resulting from transmission of the transmit signal into the target containing the analyte. In addition, the electronic circuitry includes at least one temperature sensor that detects a temperature of an element of the electronic circuitry or the antenna array.

In still another embodiment, an analyte sensor system can include an antenna array having at least three antennas each of which is configured to transmit and receive radio or microwave frequency electromagnetic waves. Electronic circuitry is connected to the antenna array and controls operation of the at least three antennas, where the electronic circuitry includes transmit side circuitry that generates a transmit signal in a radio or microwave frequency range to be transmitted by one or more of the at least three antennas into a target containing an analyte, receive side circuitry that is connectable to one or more of the at least three antennas to detect a response in the radio or microwave frequency range resulting from transmission of the transmit signal into the target containing the analyte. In addition, at least one temperature sensor is provided that detects a temperature of an element of the electronic circuitry or the antenna array.

In the non-invasive analyte sensor described herein, the receive side of the sensor can include a superheterodyne circuit. The superheterodyne circuit includes a mixer with an input that is electrically connected to a receive antenna, and a radio frequency generator connected to another input of the mixer and that is configured to generate a radio frequency signal. The mixer output is based on the input frequencies. In an example case where the inputs to the mixer are each a single frequency, the output of the mixer would be one frequency at the sum of the input frequencies and one frequency at the difference of the input frequencies. One of these is chosen as the desired frequency, and a filter, such as a band pass filter, is configured to pass the chosen frequency and reject all others. This rejects the unwanted frequency from the mixer output, and also has the added benefit of greatly reducing the noise in the system.

A calibration path may also be provided between the transmit circuit and the receive circuit that bypasses the antenna array with the transmit antenna and the receive antenna. In addition, one or more temperature sensors may be connected to various elements of the sensor, such as to the radio frequency signal generator that generates the transmitted signal and/or to the radio frequency signal generator of the superheterodyne circuit.

In one embodiment described herein, a non-invasive analyte sensor system can include a first antenna that is configured to emit radio frequency electromagnetic waves, where the first antenna is positioned and arranged to transmit a radio frequency transmit signal into a target containing at least one analyte; and a second antenna that is configured to detect radio frequency electromagnetic waves, where the second antenna is positioned and arranged to detect a radio frequency response resulting from transmission of the radio frequency transmit signal by the first antenna into the target containing the at least one analyte. A transmit circuit is electrically connectable to the first antenna, and the transmit circuit includes a first radio frequency signal generator that is configured to generate the radio frequency transmit signal to be transmitted by the first antenna. In addition, a receive circuit is electrically connectable to the second antenna, and the receive circuit includes a superheterodyne circuit.

In another embodiment described herein, a non-invasive analyte sensor system can include an antenna array having at least two antennas, or at least three antennas, each of which is configured to emit and receive radio frequency electromagnetic waves. A transmit circuit is selectively electrically connectable to any one or more of the at least two antennas, and the transmit circuit includes a first radio frequency signal generator that is configured to generate at least one transmit signal in a radio frequency range of the electromagnetic spectrum to be transmitted into a target by the one or more of the at least two antennas the transmit circuit is electrically connected to. In addition, a receive circuit is selectively electrically connectable to any one or more of the at least two antennas. The receive circuit includes a mixer with a first input that is electrically connectable to the one or more of the at least two antennas the receive circuit is electrically connected to, and a second radio frequency generator is connected to a second input of the mixer. The mixer is configured to generate a radio frequency output signal that is based on signals received via the first input and the second input, and the mixer includes an output that outputs the generated radio frequency output signal.

DRAWINGS

Like reference numbers represent like parts throughout.

DETAILED DESCRIPTION

Figure 1:
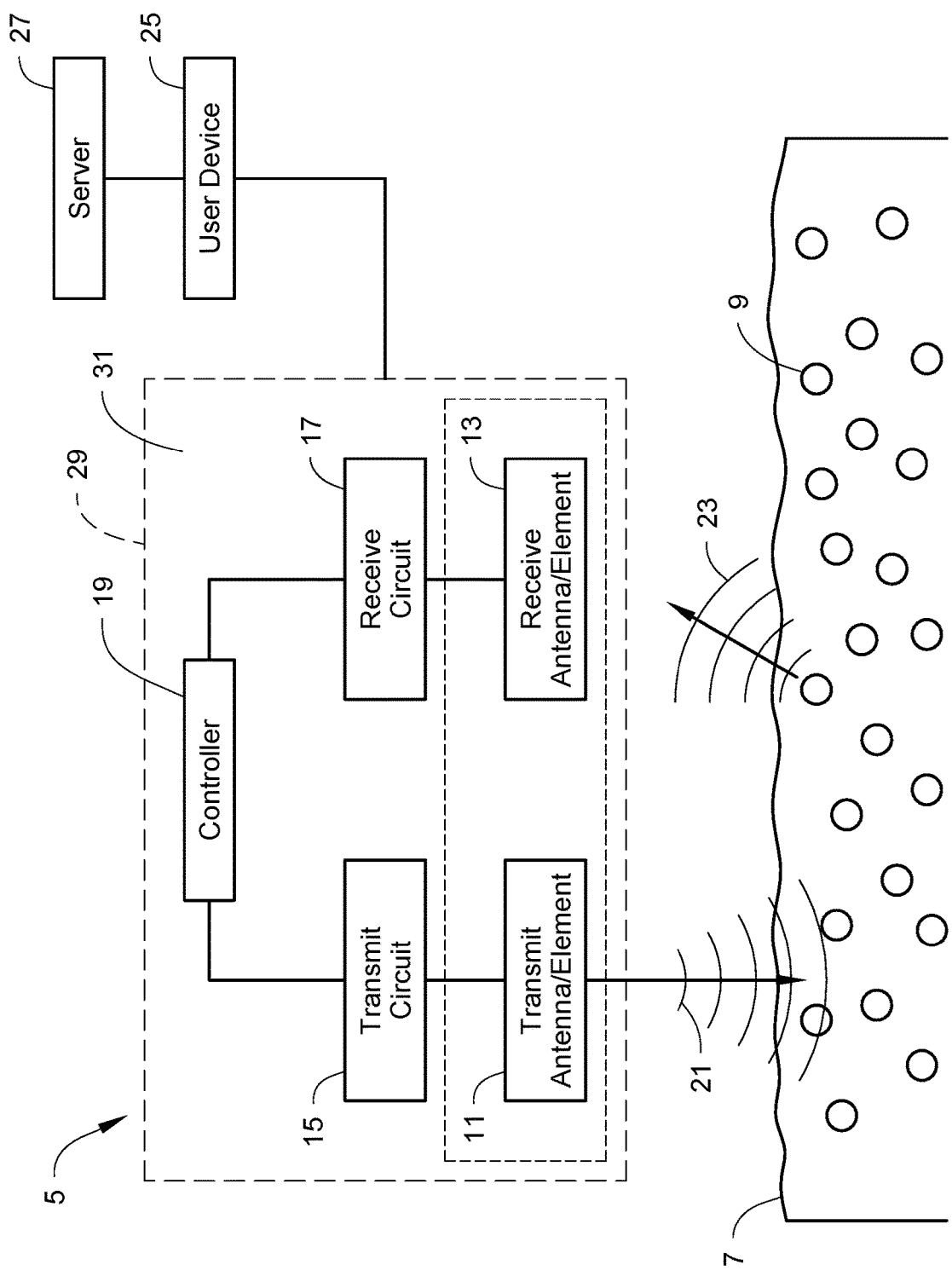
FIG. 1 is a schematic depiction of an analyte sensor system with an analyte sensor relative to a target according to an embodiment.

The following is a detailed description of apparatus, systems and methods of detecting an analyte via spectroscopic techniques using non-optical frequencies such as in the radio or microwave frequency bands of the electromagnetic spectrum. An analyte sensor described herein includes a detector array having a plurality of detector elements (also referred to as antenna elements or antennas) at least one of which can transmit an electromagnetic signal in the radio or microwave frequency range and at least one of which can receive an electromagnetic signal in the radio or microwave frequency range resulting from transmission of the electromagnetic signal. For sake of convenience, the detector array will hereinafter be referred to as an antenna array and the detector elements will hereinafter be referred to as antennas.

In one embodiment, the sensor systems described herein can be used to detect the presence of at least one analyte in a target. In another embodiment, the sensor systems described herein can detect an amount or a concentration of the at least one analyte in the target. The target can be any target containing at least one analyte of interest that one may wish to detect. The target can be human or non-human, animal or non-animal, biological or non-biological. For example, the target can include, but is not limited to, human tissue, animal tissue, plant tissue, an inanimate object, soil, a fluid, genetic material, or a microbe. Non-limiting examples of targets include, but are not limited to, a fluid, for example blood, interstitial fluid, cerebral spinal fluid, lymph fluid or urine, human tissue, animal tissue, plant tissue, an inanimate object, soil, genetic material, or a microbe. In one embodiment, the non-invasive analyte sensor described herein can simultaneously detect an analyte in both blood and in interstitial fluid. In another embodiment, the non-invasive analyte sensor described herein can simultaneously detect an analyte in blood, in interstitial fluid, and cellular material. In addition, the non-invasive analyte sensor described herein can be used without requiring any specific alignment on the human body. For example, the non-invasive analyte sensor described herein does not need to be aligned with a vein or an artery during sensing of an analyte.

The detection by the sensors described herein can be non-invasive meaning that the sensor remains outside the target, such as the human body, and the detection of the analyte occurs without requiring removal of fluid or other removal from the target, such as the human body. In the case of sensing in the human body, this non-invasive sensing may also be referred to as in vivo sensing. In other embodiments, the sensors described herein may be an in vitro sensor where the material containing the analyte has been removed, for example from a human body.

The transmit antenna and the receive antenna can be located near the target and operated as further described herein to assist in detecting at least one analyte in the target. The transmit antenna transmits a signal that is in the radio or microwave frequency range, toward and into the target. The signal with the at least two frequencies can be formed by separate signal portions, each having a discrete frequency, that are transmitted separately at separate times at each frequency. In another embodiment, the signal with the at least two frequencies may be part of a complex signal that includes a plurality of frequencies including the at least two frequencies. The complex signal can be generated by blending or multiplexing multiple signals together followed by transmitting the complex signal whereby the plurality of frequencies are transmitted at the same time. One possible technique for generating the complex signal includes, but is not limited to, using an inverse Fourier transformation technique. The receive antenna detects a response resulting from transmission of the signal by the transmit antenna into the target containing the at least one analyte of interest.

The transmit antenna and the receive antenna may be decoupled (which may also be referred to as detuned or the like) from one another. Decoupling refers to intentionally fabricating the configuration and/or arrangement of the transmit antenna and the receive antenna to minimize direct communication between the transmit antenna and the receive antenna, preferably absent shielding. Shielding between the transmit antenna and the receive antenna can be utilized. However, the transmit antenna and the receive antenna are decoupled even without the presence of shielding.

The signal(s) detected by the receive antenna can be analyzed to detect the analyte based on the intensity of the received signal(s) and reductions in intensity at one or more frequencies where the analyte absorbs the transmitted signal. An example of detecting an analyte using a non-invasive spectroscopy sensor operating in the radio or microwave frequency range of the electromagnetic spectrum is described in U.S. Pat. No. 10,548,503, the entire contents of which are incorporated herein by reference. The signal(s) detected by the receive antenna can be complex signals including a plurality of signal components, each signal component being at a different frequency. In an embodiment, the detected complex signals can be decomposed into the signal components at each of the different frequencies, for example through a Fourier transformation. In an embodiment, the complex signal detected by the receive antenna can be analyzed as a whole (i.e. without demultiplexing the complex signal) to detect the analyte as long as the detected signal provides enough information to make the analyte detection. In addition, the signal(s) detected by the receive antenna can be separate signal portions, each having a discrete frequency.

The analyte(s) can be any analyte that one may wish to detect. The analyte can be human or non-human, animal or non-animal, biological or non-biological. For example, the analyte(s) can include, but is not limited to, one or more of blood glucose, blood alcohol, white blood cells, or luteinizing hormone. The analyte(s) can include, but is not limited to, a chemical, a combination of chemicals, a virus, a bacteria, or the like. The analyte can be a chemical included in another medium, with non-limiting examples of such media including a fluid containing the at least one analyte, for example blood, interstitial fluid, cerebral spinal fluid, lymph fluid or urine, human tissue, animal tissue, plant tissue, an inanimate object, soil, genetic material, or a microbe. The analyte(s) may also be a non-human, non-biological particle such as a mineral or a contaminant.

The analyte(s) can include, for example, naturally occurring substances, artificial substances, metabolites, and/or reaction products. As non-limiting examples, the at least one analyte can include, but is not limited to, insulin, acarboxyprothrombin; acylcarnitine; adenine phosphoribosyl transferase; adenosine deaminase; albumin; alpha-fetoprotein; amino acid profiles (arginine (Krebs cycle), histidine/urocanic acid, homocysteine, phenylalanine/tyrosine, tryptophan); andrenostenedione; antipyrine; arabinitol enantiomers; arginase; benzoylecgonine (cocaine); biotinidase; biopterin; c-reactive protein; carnitine; pro-BNP; BNP; troponin; carnosinase; CD4; ceruloplasmin; chenodeoxycholic acid; chloroquine; cholesterol; cholinesterase; conjugated 1-β hydroxy-cholic acid; cortisol; creatine kinase; creatine kinase MM isoenzyme; cyclosporin A; d-penicillamine; de-ethylchloroquine; dehydroepiandrosterone sulfate; DNA (acetylator polymorphism, alcohol dehydrogenase, alpha 1-antitrypsin, cystic fibrosis, Duchenne/Becker muscular dystrophy, analyte-6-phosphate dehydrogenase, hemoglobin A, hemoglobin S, hemoglobin C, hemoglobin D, hemoglobin E, hemoglobin F, D-Punjab, beta-thalassemia, hepatitis B virus, HCMV, HIV-1, HTLV-1, Leber hereditary optic neuropathy, MCAD, RNA, PKU, *Plasmodium vivax*, sexual differentiation, 21-deoxycortisol); desbutylhalofantrine; dihydropteridine reductase; diptheria/tetanus antitoxin; erythrocyte arginase; erythrocyte protoporphyrin; esterase D; fatty acids/acylglycines; free β-human chorionic gonadotropin; free erythrocyte porphyrin; free thyroxine (FT4); free tri-iodothyronine (FT3); fumarylacetoacetase; galactose/gal-1-phosphate; galactose-1-phosphate uridyltransferase; gentamicin; analyte-6-phosphate dehydrogenase; glutathione; glutathione perioxidase; glycocholic acid; glycosylated hemoglobin; halofantrine; hemoglobin variants; hexosaminidase A; human erythrocyte carbonic anhydrase I; 17-alpha-hydroxyprogesterone; hypoxanthine phosphoribosyl transferase; immunoreactive trypsin; lactate; lead; lipoproteins ((a), B/A-1, β); lysozyme; mefloquine; netilmicin; phenobarbitone; phenytoin; phytanic/pristanic acid; progesterone; prolactin; prolidase; purine nucleoside phosphorylase; quinine; reverse tri-iodothyronine (rT3); selenium; serum pancreatic lipase; sissomicin; somatomedin C; specific antibodies (adenovirus, anti-nuclear antibody, anti-zeta antibody, arbovirus, Aujeszky's disease virus, dengue virus, *Dracunculus medinensis, Echinococcus granulosus, Entamoeba histolytica*, enterovirus, *Giardia duodenalisa, Helicobacter pylori*, hepatitis B virus, herpes virus, HIV-1, IgE (atopic disease), influenza virus, *Leishmania donovani*, leptospira, measles/mumps/rubella, *Mycobacterium leprae, Mycoplasma pneumoniae, Myoglobin, Onchocerca volvulus*, parainfluenza virus, *Plasmodium falciparum*, polio virus, *Pseudomonas aeruginosa*, respiratory syncytial virus, *rickettsia* (scrub typhus), *Schistosoma mansoni, Toxoplasma gondii, Trepenoma pallidium, Trypanosoma cruzi*/rangeli, vesicular *stomatis* virus, *Wuchereria bancrofti*, yellow fever virus); specific antigens (hepatitis B virus, HIV-1); succinylacetone; sulfadoxine; theophylline; thyrotropin (TSH); thyroxine (T4); thyroxine-binding globulin; trace elements; transferrin; UDP-galactose-4-epimerase; urea; uroporphyrinogen I synthase; vitamin A; white blood cells; and zinc protoporphyrin.

The analyte(s) can also include one or more chemicals introduced into the target. The analyte(s) can include a marker such as a contrast agent, a radioisotope, or other chemical agent. The analyte(s) can include a fluorocarbon-based synthetic blood. The analyte(s) can include a drug or pharmaceutical composition, with non-limiting examples including ethanol; *cannabis* (marijuana, tetrahydrocannabinol, hashish); inhalants (nitrous oxide, amyl nitrite, butyl nitrite, chlorohydrocarbons, hydrocarbons); cocaine (crack cocaine); stimulants (amphetamines, methamphetamines, Ritalin, Cylert, Preludin, Didrex, PreState, Voranil, Sandrex, Plegine); depressants (barbiturates, methaqualone, tranquilizers such as Valium, Librium, Miltown, Serax, Equanil, Tranxene); hallucinogens (phencyclidine, lysergic acid, mescaline, peyote, psilocybin); narcotics (heroin, codeine, morphine, opium, meperidine, Percocet, Percodan, Tussionex, Fentanyl, Darvon, Talwin, Lomotil); designer drugs (analogs of fentanyl, meperidine, amphetamines, methamphetamines, and phencyclidine, for example, Ecstasy); anabolic steroids; and nicotine. The analyte(s) can include other drugs or pharmaceutical compositions. The analyte(s) can include neurochemicals or other chemicals generated within the body, such as, for example, ascorbic acid, uric acid, dopamine, noradrenaline, 3-methoxytyramine (3MT), 3,4-Dihydroxyphenylacetic acid (DOPAC), Homovanillic acid (HVA), 5-Hydroxytryptamine (5HT), and 5-Hydroxyindoleacetic acid (FHIAA).

Referring now to FIG. 1, an embodiment of a non-invasive analyte sensor system with a non-invasive analyte sensor 5 is illustrated. The sensor 5 is depicted relative to a target 7 that contains an analyte of interest 9, for example an analyte in interstitial fluid in a human body. In this example, the sensor 5 is depicted as including an antenna array that includes a transmit antenna/element 11 (hereinafter "transmit antenna 11") and a receive antenna/element 13 (hereinafter "receive antenna 13"). The sensor 5 further includes a transmit circuit 15, a receive circuit 17, and a controller 19. As discussed further below, the sensor 5 can also include a power supply, such as a battery (not shown in FIG. 1). In some embodiments, power can be provided from mains power, for example by plugging the sensor 5 into a wall socket via a cord connected to the sensor 5.

The transmit antenna 11 is positioned, arranged and configured to transmit a signal 21 that is the radio frequency (RF) or microwave range of the electromagnetic spectrum into the target 7. The transmit antenna 11 can be an electrode or any other suitable transmitter of electromagnetic signals in the radio frequency (RF) or microwave range. The transmit antenna 11 can have any arrangement and orientation relative to the target 7 that is sufficient to allow the analyte sensing to take place. In one non-limiting embodiment, the transmit antenna 11 can be arranged to face in a direction that is substantially toward the target 7.

The signal 21 transmitted by the transmit antenna 11 is generated by the transmit circuit 15 which is electrically connectable to the transmit antenna 11. The transmit circuit 15 can have any configuration that is suitable to generate a transmit signal to be transmitted by the transmit antenna 11. Transmit circuits for generating transmit signals in the RF or microwave frequency range are well known in the art. In one embodiment, the transmit circuit 15 can include, for example, a connection to a power source, a frequency generator, and optionally filters, amplifiers or any other suitable elements for a circuit generating an RF or microwave frequency electromagnetic signal. In an embodiment, the signal generated by the transmit circuit 15 can have at least two discrete frequencies (i.e. a plurality of discrete frequencies), each of which is in the range from about 10 kHz to about 100 GHz. In another embodiment, each of the at least two discrete frequencies can be in a range from about 300 MHz to about 6000 MHz. In an embodiment, the transmit circuit 15 can be configured to sweep through a range of frequencies that are within the range of about 10 kHz to about 100 GHz, or in another embodiment a range of about 300 MHZ to about 6000 MHz. In an embodiment, the transmit circuit 15 can be configured to produce a complex transmit signal, the complex signal including a plurality of signal components, each of the signal components having a different frequency. The complex signal can be generated by blending or multiplexing multiple signals together followed by transmitting the complex signal whereby the plurality of frequencies are transmitted at the same time.

The receive antenna 13 is positioned, arranged, and configured to detect one or more electromagnetic response signals 23 that result from the transmission of the transmit signal 21 by the transmit antenna 11 into the target 7 and impinging on the analyte 9. The receive antenna 13 can be an electrode or any other suitable receiver of electromagnetic signals in the radio frequency (RF) or microwave range. In an embodiment, the receive antenna 13 is configured to detect electromagnetic signals having at least two frequencies, each of which is in the range from about 10 kHz to about 100 GHz, or in another embodiment a range from about 300 MHz to about 6000 MHz. The receive antenna 13 can have any arrangement and orientation relative to the target 7 that is sufficient to allow detection of the response signal(s) 23 to allow the analyte sensing to take place. In one non-limiting embodiment, the receive antenna 13 can be arranged to face in a direction that is substantially toward the target 7.

The receive circuit 17 is electrically connectable to the receive antenna 13 and conveys the received response from the receive antenna 13 to the controller 19. The receive circuit 17 can have any configuration that is suitable for interfacing with the receive antenna 13 to convert the electromagnetic energy detected by the receive antenna 13 into one or more signals reflective of the response signal(s) 23. The construction of receive circuits are well known in the art. The receive circuit 17 can be configured to condition the signal(s) prior to providing the signal(s) to the controller 19, for example through amplifying the signal(s), filtering the signal(s), or the like. Accordingly, the receive circuit 17 may include filters, amplifiers, or any other suitable components for conditioning the signal(s) provided to the controller 19. In an embodiment, at least one of the receive circuit 17 or the controller 19 can be configured to decompose or demultiplex a complex signal, detected by the receive antenna 13, including a plurality of signal components each at different frequencies into each of the constituent signal components. In an embodiment, decomposing the complex signal can include applying a Fourier transform to the detected complex signal. However, decomposing or demultiplexing a received complex signal is optional. Instead, in an embodiment, the complex signal detected by the receive antenna can be analyzed as a whole (i.e. without demultiplexing the complex signal) to detect the analyte as long as the detected signal provides enough information to make the analyte detection.

The controller 19 controls the operation of the sensor 5. The controller 19, for example, can direct the transmit circuit 15 to generate a transmit signal to be transmitted by the transmit antenna 11. The controller 19 further receives signals from the receive circuit 17. The controller 19 can optionally process the signals from the receive circuit 17 to detect the analyte(s) 9 in the target 7. In one embodiment, the controller 19 may optionally be in communication with at least one external device 25 such as a user device and/or a remote server 27, for example through one or more wireless connections such as Bluetooth, wireless data connections such a 4G, 5G, LTE or the like, or Wi-Fi. If provided, the external device 25 and/or remote server 27 may process (or further process) the signals that the controller 19 receives from the receive circuit 17, for example to detect the analyte(s) 9. If provided, the external device 25 may be used to provide communication between the sensor 5 and the remote server 27, for example using a wired data connection or via a wireless data connection or Wi-Fi of the external device 25 to provide the connection to the remote server 27.

With continued reference to FIG. 1, the sensor 5 may include a sensor housing 29 (shown in dashed lines) that defines an interior space 31. Components of the sensor 5 may be attached to and/or disposed within the housing 29. For example, the transmit antenna 11 and the receive antenna 13 are attached to the housing 29. In some embodiments, the antennas 11, 13 may be entirely or partially within the interior space 31 of the housing 29. In some embodiments, the antennas 11, 13 may be attached to the housing 29 but at least partially or fully located outside the interior space 31. In some embodiments, the transmit circuit 15, the receive circuit 17 and the controller 19 are attached to the housing 29 and disposed entirely within the sensor housing 29.

The receive antenna 13 may be decoupled or detuned with respect to the transmit antenna 11 such that electromagnetic coupling between the transmit antenna 11 and the receive antenna 13 is reduced. The decoupling of the transmit antenna 11 and the receive antenna 13 increases the portion of the signal(s) detected by the receive antenna 13 that is the response signal(s) 23 from the target 7, and minimizes direct receipt of the transmitted signal 21 by the receive antenna 13. The decoupling of the transmit antenna 11 and the receive antenna 13 results in transmission from the transmit antenna 11 to the receive antenna 13 having a reduced forward gain (S21) and an increased reflection at output (S22) compared to antenna systems having coupled transmit and receive antennas.

In an embodiment, coupling between the transmit antenna 11 and the receive antenna 13 is 95% or less. In another embodiment, coupling between the transmit antenna 11 and the receive antenna 13 is 90% or less. In another embodiment, coupling between the transmit antenna 11 and the receive antenna 13 is 85% or less. In another embodiment, coupling between the transmit antenna 11 and the receive antenna 13 is 75% or less.

Any technique for reducing coupling between the transmit antenna 11 and the receive antenna 13 can be used. For example, the decoupling between the transmit antenna 11 and the receive antenna 13 can be achieved by one or more intentionally fabricated configurations and/or arrangements between the transmit antenna 11 and the receive antenna 13 that is sufficient to decouple the transmit antenna 11 and the receive antenna 13 from one another.

For example, in one embodiment described further below, the decoupling of the transmit antenna 11 and the receive antenna 13 can be achieved by intentionally configuring the transmit antenna 11 and the receive antenna 13 to have different geometries from one another. Intentionally different geometries refers to different geometric configurations of the transmit and receive antennas 11, 13 that are intentional. Intentional differences in geometry are distinct from differences in geometry of transmit and receive antennas that may occur by accident or unintentionally, for example due to manufacturing errors or tolerances.

Another technique to achieve decoupling of the transmit antenna 11 and the receive antenna 13 is to provide appropriate spacing between each antenna 11, 13 that is sufficient to decouple the antennas 11, 13 and force a proportion of the electromagnetic lines of force of the transmitted signal 21 into the target 7 thereby minimizing or eliminating as much as possible direct receipt of electromagnetic energy by the receive antenna 13 directly from the transmit antenna 11 without traveling into the target 7. The appropriate spacing between each antenna 11, 13 can be determined based upon factors that include, but are not limited to, the output power of the signal from the transmit antenna 11, the size of the antennas 11, 13, the frequency or frequencies of the transmitted signal, and the presence of any shielding between the antennas. This technique helps to ensure that the response detected by the receive antenna 13 is measuring the analyte 9 and is not just the transmitted signal 21 flowing directly from the transmit antenna 11 to the receive antenna 13. In some embodiments, the appropriate spacing between the antennas 11, 13 can be used together with the intentional difference in geometries of the antennas 11, 13 to achieve decoupling.

In one embodiment, the transmit signal that is transmitted by the transmit antenna 11 can have at least two different frequencies, for example upwards of 7 to 12 different and discrete frequencies. In another embodiment, the transmit signal can be a series of discrete, separate signals with each separate signal having a single frequency or multiple different frequencies.

In one embodiment, the transmit signal (or each of the transmit signals) can be transmitted over a transmit time that is less than, equal to, or greater than about 300 ms. In another embodiment, the transmit time can be than, equal to, or greater than about 200 ms. In still another embodiment, the transmit time can be less than, equal to, or greater than about 30 ms. The transmit time could also have a magnitude that is measured in seconds, for example 1 second, 5 seconds, 10 seconds, or more. In an embodiment, the same transmit signal can be transmitted multiple times, and then the transmit time can be averaged. In another embodiment, the transmit signal (or each of the transmit signals) can be transmitted with a duty cycle that is less than or equal to about 50%.

The interaction between the transmitted signal and the analyte may, in some cases, increase the intensity of the signal(s) that is detected by the receive antenna, and may, in other cases, decrease the intensity of the signal(s) that is detected by the receive antenna. For example, in one non-limiting embodiment, when analyzing the detected response, compounds in the target, including the analyte of interest that is being detected, can absorb some of the transmit signal, with the absorption varying based on the frequency of the transmit signal. The response signal detected by the receive antenna may include drops in intensity at frequencies where compounds in the target, such as the analyte, absorb the transmit signal. The frequencies of absorption are particular to different analytes. The response signal(s) detected by the receive antenna can be analyzed at frequencies that are associated with the analyte of interest to detect the analyte based on drops in the signal intensity corresponding to absorption by the analyte based on whether such drops in signal intensity are observed at frequencies that correspond to the absorption by the analyte of interest. A similar technique can be employed with respect to increases in the intensity of the signal(s) caused by the analyte.

Detection of the presence of the analyte can be achieved, for example, by identifying a change in the signal intensity detected by the receive antenna at a known frequency associated with the analyte. The change may be a decrease in the signal intensity or an increase in the signal intensity depending upon how the transmit signal interacts with the analyte. The known frequency associated with the analyte can be established, for example, through testing of solutions known to contain the analyte. Determination of the amount of the analyte can be achieved, for example, by identifying a magnitude of the change in the signal at the known frequency, for example using a function where the input variable is the magnitude of the change in signal and the output variable is an amount of the analyte. The determination of the amount of the analyte can further be used to determine a concentration, for example based on a known mass or volume of the target. In an embodiment, presence of the analyte and determination of the amount of analyte may both be determined, for example by first identifying the change in the detected signal to detect the presence of the analyte, and then processing the detected signal(s) to identify the magnitude of the change to determine the amount.

Further information on the sensor 5 and its components and variations thereof can be found in U.S. Pat. Nos. 11,063,373, 11,031,970, 11,058,317, 11,058,331 and 11,033,208 the entire contents of which are incorporated herein by reference in their entirety.

Figure 2:
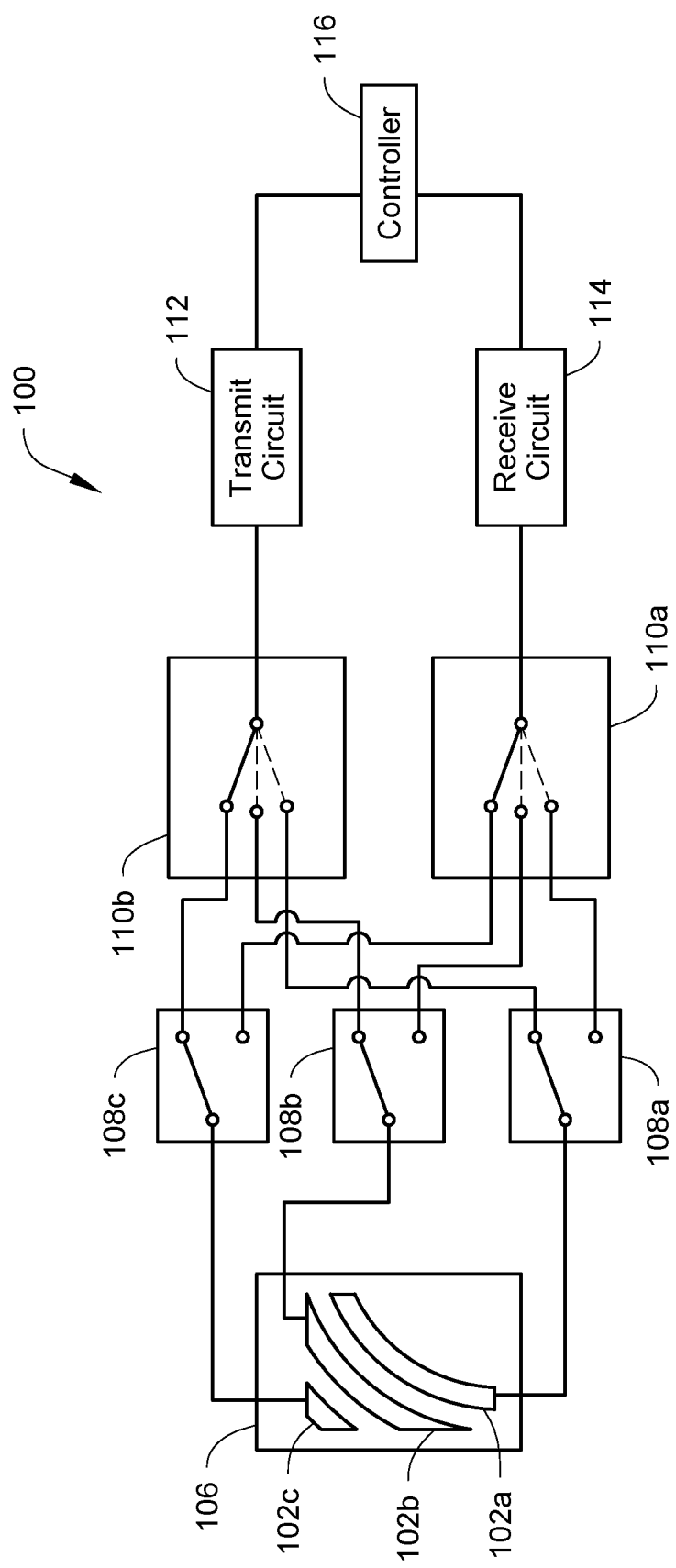
FIG. 2 is a schematic depiction of an embodiment of a non-invasive analyte sensor system with an antenna array having three antennas.
Figure 3:
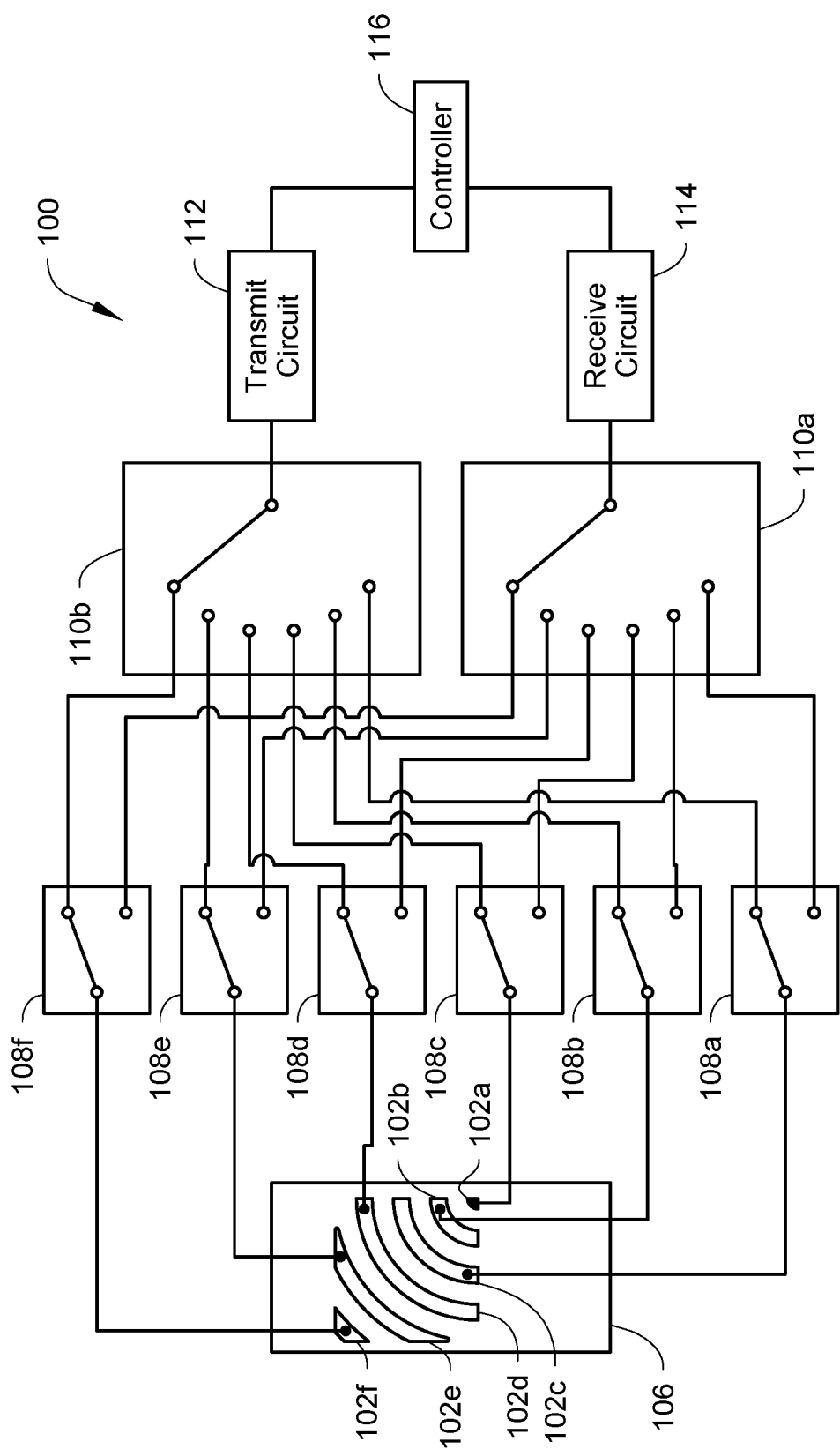
FIG. 3 is a schematic depiction of another embodiment of a non-invasive analyte sensor system with an antenna array having six antennas.

FIGS. 2-3 are schematic depictions of additional embodiments of a non-invasive analyte sensor system 100. The systems 100 depicted in FIGS. 2-3 includes at least three or more antennas (FIG. 2) or at least six or more antennas (FIG. 3). However, a different number of antennas can be used. In each of the embodiments, the system 100 is configured so that one or more of the antennas of the antenna array can be used as either a transmit antenna or as a receive antenna. In FIGS. 2-3, like elements are referenced using the same reference numerals. As with the previously described embodiment in FIG. 1, the antenna arrays in FIGS. 2-3 can be a decoupled antenna array and the antennas of the antenna array can be decoupled from one another. However, in some embodiments, the antennas of the system 100 may not be decoupled from one another. In one embodiment, the antennas used in the arrays in FIGS. 2-3 can have different geometries from each other.

In the embodiment in FIG. 2, the antenna array of the system 100 has three antennas 102*a*, 102*b*, 102*c* each of which is disposed on a substrate 106. The system further includes three switches 108*a*, 108*b*, 108*c*, a receive switch controller 110*a*, a transmit switch controller 110*b* separate from the receive switch controller 110*a*, a transmit circuit 112, a receive circuit 114, and a controller 116. In the embodiment in FIG. 3, the antenna array of the system 100 has six antennas 102*a-f* each of which is disposed on the substrate 106, and six of the switches 108*a-f*. Further information on the system 100 in FIGS. 2 and 3 can be found in U.S. Pat. No. 11,058,321, the entire contents of which are incorporated herein by reference.

Figure 4:
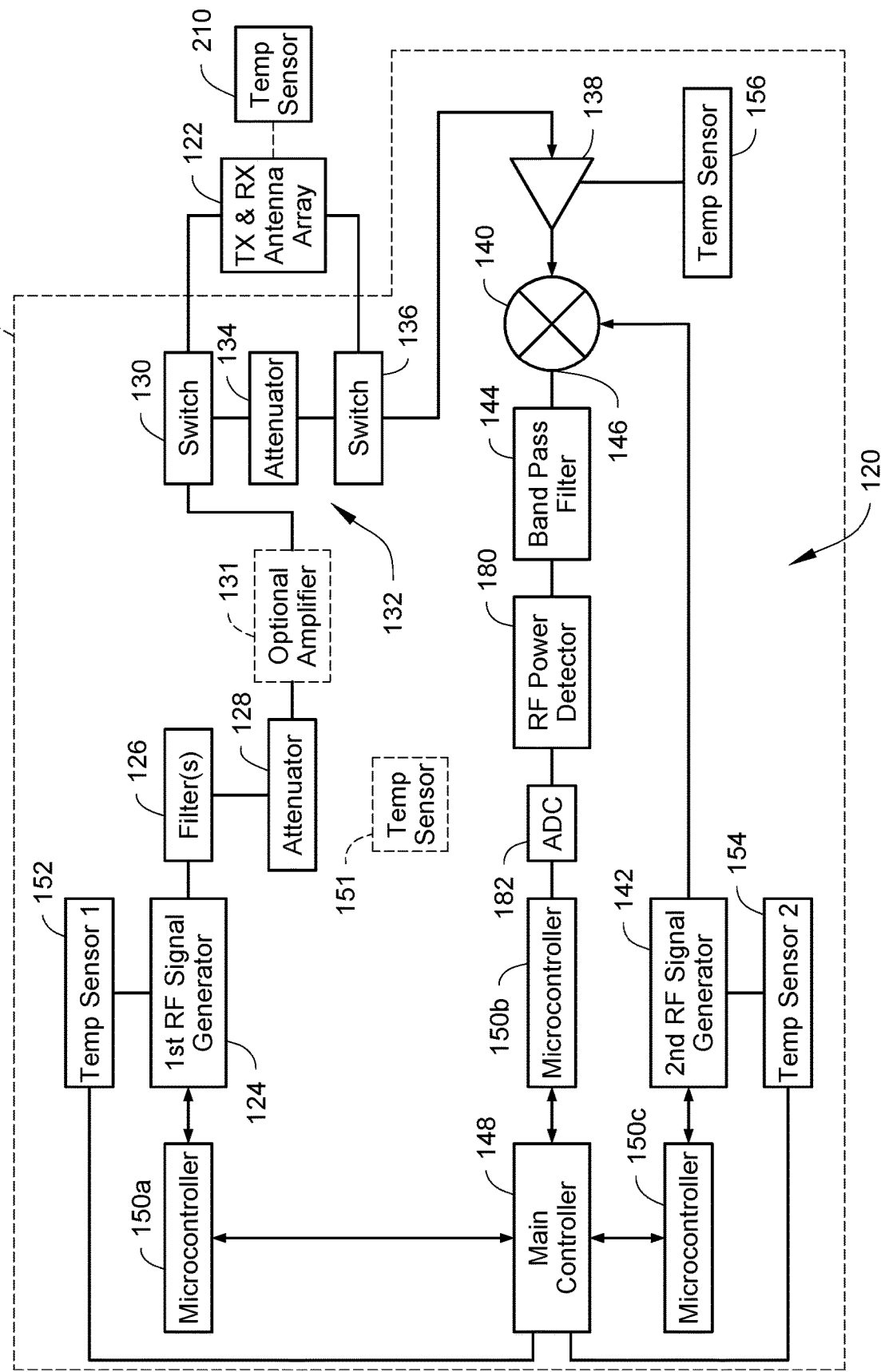
FIG. 4 is a schematic depiction of an embodiment of a circuit used in the analyte sensor with a superheterodyne circuit on the receive side.

Referring now to FIG. 4, an example of an analyte sensor system 120 is depicted having an antenna array 122 having a plurality of antennas (not shown). The array 122 can be similar to the antenna arrays in FIGS. 2 and 3 or it can have a different configuration with a different number of antennas. The system 120 includes transmit side circuitry that includes a first radio frequency (RF) signal generator 124, one or more filters 126, and one or more switches 130. An optional transmit amplifier 131 may also be provided. The RF signal generator 124 generates a radio frequency signal to be transmitted. The RF signal generated by the signal generator 124 can have a frequency that is in a range from about 10 kHz to about 100 GHz, or in a range from about 300 MHz to about 6000 MHz. The filter(s) 126 receives the signal generated by the signal generator 124 and filters the signal to remove harmonic content. One or more attenuators 128 can be provided at various locations in the system 120 for impedance matching/stabilization of the RF signal. The signal may then be amplified by the optional transmit amplifier 131 to a level appropriate to detect or measure the analyte. The signal is then directed into the switch(es) 130 which directs the signal to any one or more of the antennas of the array 122 to transmit the signal, or directs the signal onto a calibration path 132 that bypasses the antenna array 122 to receive side circuitry. The calibration path 132 represents the measurement of a known quantity for the purposes of system calibration and test, and in this case can include an attenuator 134. The calibration path 132 provides a known value of measurement which is determined by the attenuator 134.

The receive side circuitry includes one or more switches 136 which can selectively connect to any one or more of the antennas of the array 122 to act as a receive antenna. The received signal is then input to an amplifier 138, such as a low noise amplifier. The amplified signal is then fed into an input of a mixer 140 which forms part of a superheterodyne circuit along with a second RF signal generator 142 and a band pass filter 144. The mixer 140 is fed with the amplified signal from the amplifier 138 via one input, and is fed with a second RF signal generated by the RF signal generator 142 (also referred to as a local oscillator). The frequency of the signal output from the RF signal generator 142 may be a fixed frequency, and the frequency is offset from the frequency of the transmitted signal that is transmitted by the one or more transmit antennas. The mixer 140 includes an output 146 which outputs an output signal that is based on the input frequencies from the amplifier 138 and the RF signal generator 142. In an example case where the inputs to the mixer 140 are each a single frequency, the output of the mixer 140 would be one frequency at the sum of the input frequencies from the amplifier 138 and the RF signal generator 142 and one frequency at the difference of the input frequencies. One of these frequencies is chosen as the desired frequency, and the band pass filter 144 is configured to pass the chosen frequency and reject all others.

The output of the band pass filter 144 is then processed by an RF power detector 180 and sampled or digitized by an analog to digital converter (ADC) 182. The RF power detector 180 can be any type of detector that is suitable for detecting the RF power output from the band pass filter 144. In one non-limiting example, the RF power detector 180 can be a log amplifier. The RF power detector 180 and the ADC 182 can be implemented as discrete circuits as illustrated, integrated into the microcontroller 150*b* described below, integrated into the band pass filter 144, integrated together, or one integrated into the band pass filter 144 and one integrated into the microcontroller 150*b*.

The system 120 can further include a main controller 148 that communicates with and can control microcontrollers 150*a*. 150*b*, 150*c* that are connected to and control the signal generator 124, the RF power detector 180, the ADC 182, and the signal generator 142.

In another embodiment, one or more temperature sensors can be provided to sense the temperature of one or more components on the transmit side and/or on the receive side. In general, referring to FIG. 7, a non-invasive analyte sensor system 200 is depicted that can include an antenna array 202 and control circuitry 204 that controls operation of the antenna array 202. The antenna array 202 can be similar to the antenna arrays in FIGS. 2 and 3 or it can have a different configuration with a different number of antennas. The control circuitry 204 can have any configuration suitable for controlling the operation of the antenna array in the manner described herein. For example, the control circuitry 204 can have a construction like depicted in any one of FIGS. 2-6. The control circuitry 204 includes one or more temperature sensors 206 that senses the temperature of corresponding ones of elements of the control circuitry 204. The element of the control circuitry 204 whose temperature is sensed can be, but is not limited to, one or more of a circuit board of the control circuitry 204, a signal generator, a radio frequency power detector, and an amplifier. The sensed temperature(s) of the element can be used to post-process (i.e. correct) the data collected by the analyte sensor 200 and/or used to adjust operation of the analyte sensor 200.

To help explain the concept of the temperature sensor, reference will be made to FIGS. 4-6. For example, referring to FIG. 4, a temperature sensor 151 can be provided on a circuit board 208 on which the various electronic components of the transmit side circuitry and the receive side circuitry are mounted in order to sense the temperature of the circuit board 208. Not all of the elements need to be mounted on the circuit board 208. For example, certain elements such as the main controller 148 and/or one or more of the microcontrollers 150a, 150b, 150c can be mounted at one or more locations separate from the circuit board. In one embodiment, the antenna array 122 may be mounted on the circuit board 208. In another embodiment, the antenna array 122 can include a temperature sensor 210 to sense the temperature of the antenna array 122 for use in post-processing the data and/or used to adjust operation of the analyte sensor 200.

In addition or alternatively, a temperature sensor 152 can be provided to sense the temperature of the signal generator 124 and/or a temperature sensor 154 can be provided to sense the temperature of the signal generator 142. In another embodiment, a temperature sensor 156 can be associated with the amplifier 138 to sense the temperature of the amplifier 138. The sensed temperature(s) can be fed to the main controller 148 (or to one or more of the microcontrollers 150a-c), and the main controller 148 (or one of the microcontrollers 150a-c) can run a temperature compensation algorithm. In one embodiment, the temperature compensation algorithm can be used to post-process (i.e. correct) the data being measured with the aid of the calibration path 132 and/or previous known measurements or calculated coefficients that account for the effects of temperature. In another embodiment, the sensed temperature(s) can be used to adjust operation of the system such as the operation of the signal generator(s) 124, 142, based on the sensed temperature(s).

Figure 5:
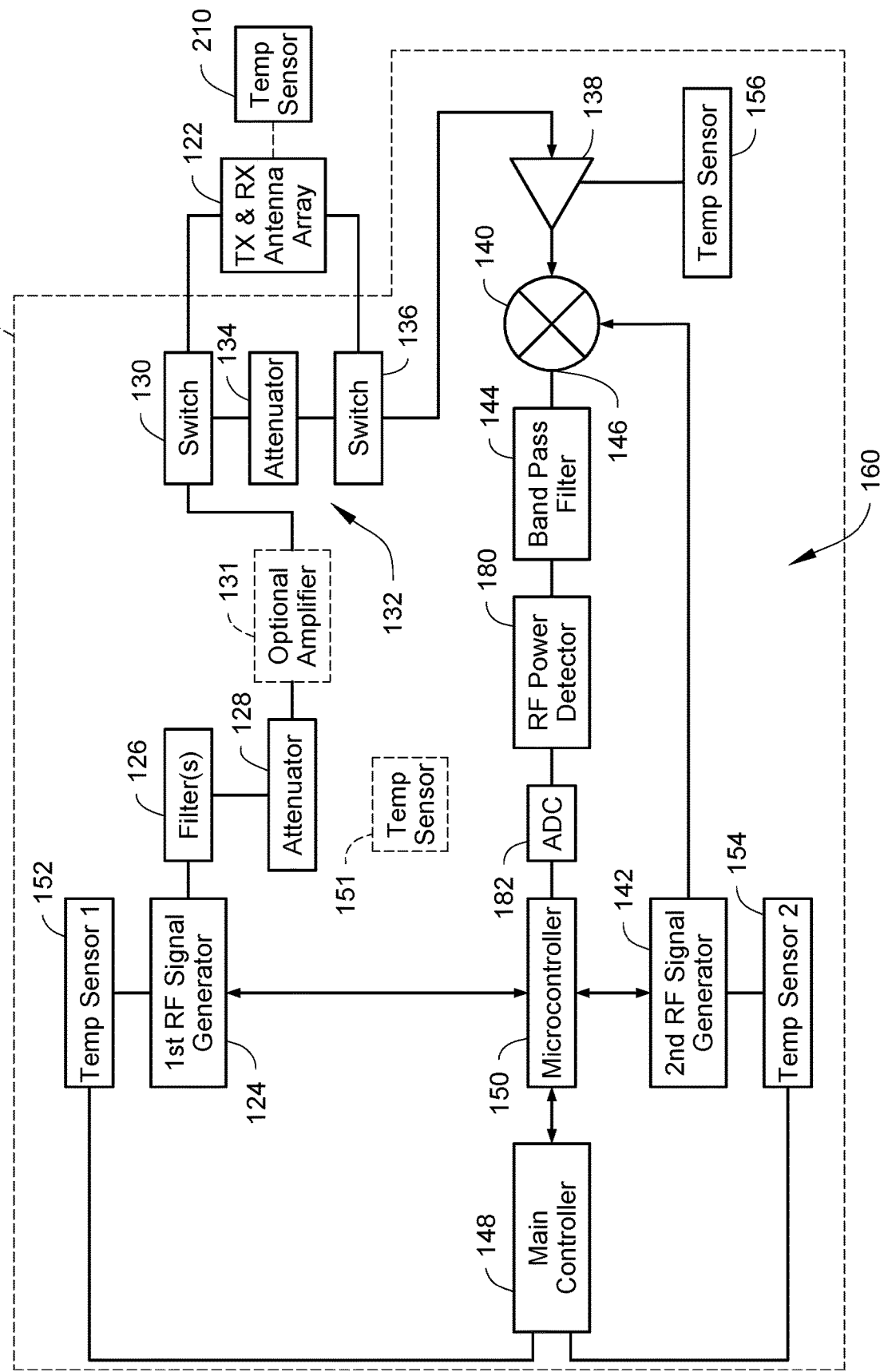
FIG. 5 is a schematic depiction of another embodiment of a circuit used in the analyte sensor with a superheterodyne circuit on the receive side.

FIG. 5 depicts another example of an analyte sensor system 160 that includes a superheterodyne circuit. The system 160 in FIG. 5 is similar to the system 120 in FIG. 4, and elements in FIG. 5 that are similar to or the same as elements in FIG. 4 are referenced using the same reference numerals. The system 160 differs from the system 120 in that the system 160 uses a single microcontroller 150 that is connected to and controls each of the signal generator 124, the signal generator 142, and the detection circuitry of the RF power detector 180 and the ADC 182. The system 160 may otherwise be the same as the system 120.

Figure 6:
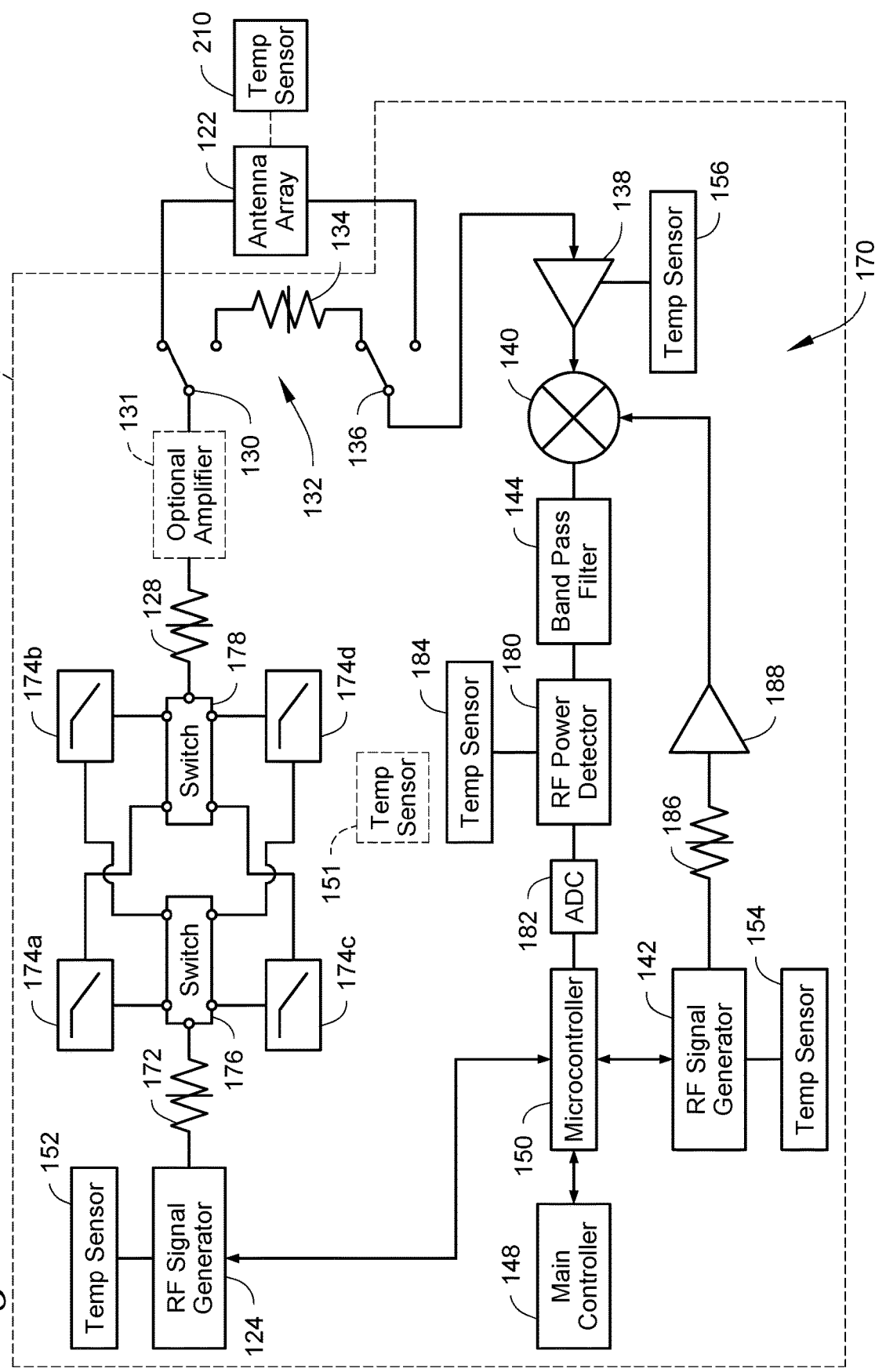
FIG. 6 is a schematic depiction of another embodiment of a circuit used in the analyte sensor with a superheterodyne circuit on the receive side.
Figure 7:
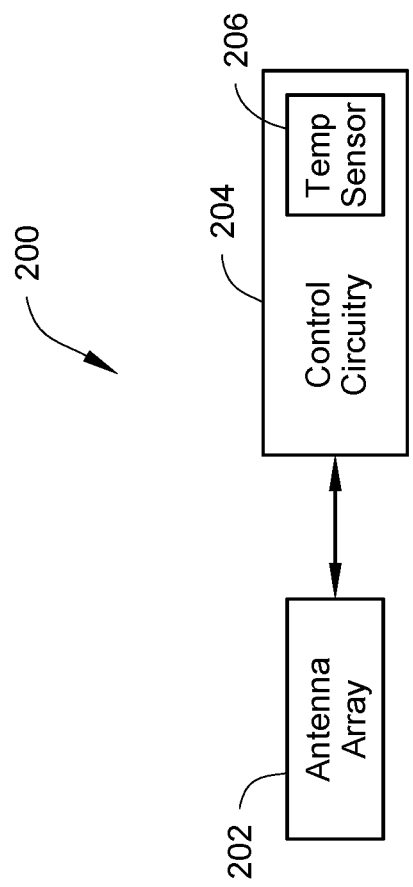
FIG. 7 is a schematic depiction of another embodiment of an analyte sensor system with one or more temperature sensors.

FIG. 6 depicts another example of an analyte sensor system 170 that includes a superheterodyne circuit. The system 170 in FIG. 6 is similar to the systems 120, 160 in FIGS. 4 and 5, and elements in FIG. 6 that are similar to or the same as elements in FIGS. 4 and 5 are referenced using the same reference numerals. The system 170 includes transmit side circuitry that includes the RF signal generator 124, an attenuator 172 for impedance matching, a plurality of filters 174a, 174b, 174c, 174d, switches 176, 178 for directing the signal to and from the appropriate filter 174a-d, the attenuator 128, and the one or more switches 130.

The receive side circuitry includes the one or more switches 136, the amplifier 138, the mixer 140, the second RF signal generator 142, and the band pass filter 144. In addition, the receive side circuitry includes the RF power detector 180, and the ADC 182. In this embodiment, a temperature sensor 184 that has a function similar to the temperature sensors 151, 152, 154, 156 may also be provided to sense the temperature of the RF power detector 180 which is then fed into the main controller 148 or to the microcontroller 150. In addition, an attenuator 186 for impedance matching and an amplifier 188 may be provided between the signal generator 142 and the mixer 140 to properly condition the RF signal fed into the second input of the mixer 140.

The terminology used in this specification is intended to describe particular embodiments and is not intended to be limiting. The terms "a," "an," and "the" include the plural forms as well, unless clearly indicated otherwise. The terms "comprises" and/or "comprising," when used in this specification, specify the presence of the stated features, integers, steps, operations, elements, and/or components, but do not preclude the presence or addition of one or more other features, integers, steps, operations, elements, and/or components.

The examples disclosed in this application are to be considered in all respects as illustrative and not limitative. The scope of the invention is indicated by the appended claims rather than by the foregoing description; and all changes which come within the meaning and range of equivalency of the claims are intended to be embraced therein.

The invention claimed is:

1. An analyte sensor system, comprising:
an antenna array having at least three antennas each of which is configured to transmit and receive radio or microwave frequency electromagnetic waves;
electronic circuitry connected to the antenna array and controlling operation of the at least three antennas so that any one or more of the at least three antennas can be controlled to transmit a transmit signal in a radio or microwave frequency range into a target containing an analyte and so that any one or more of the at least three antennas can be controlled to detect a response in the radio or microwave frequency range resulting from transmission of the transmit signal into the target containing the analyte; and
the electronic circuitry includes at least one temperature sensor that detects a temperature of an element of the electronic circuitry;
wherein the electronic circuitry includes a signal generator, a radio frequency power detector, and an amplifier, and the at least one temperature sensor detects a temperature of the signal generator, the radio frequency power detector, or the amplifier.

2. The analyte sensor system of claim 1, wherein the at least one analyte comprises glucose, alcohol, white blood cells, or luteinizing hormone.

3. An analyte sensor system, comprising:
an antenna array having at least three antennas each of which is configured to transmit and receive radio or microwave frequency electromagnetic waves;
electronic circuitry connected to the antenna array and controlling operation of the at least three antennas, the electronic circuitry includes:
transmit side circuitry that generates a transmit signal in a radio or microwave frequency range to be transmitted by one or more of the at least three antennas into a target containing an analyte;
receive side circuitry that is connectable to one or more of the at least three antennas to detect a response in the radio or microwave frequency range resulting from transmission of the transmit signal into the target containing the analyte; and
at least one temperature sensor that detects a temperature of an element of the electronic circuitry;
wherein the receive side circuitry includes a signal generator, a radio frequency power detector, and an amplifier, and the at least one temperature sensor detects a temperature of the signal generator, the radio frequency power detector, or the amplifier.

4. The analyte sensor system of claim 3, wherein the at least one analyte comprises glucose, alcohol, white blood cells, or luteinizing hormone.

* * * * *